US00PP24297P3

(12) United States Plant Patent
Reimer

(10) Patent No.: US PP24,297 P3
(45) Date of Patent: Mar. 11, 2014

(54) NECTARINE PLANT NAMED 'R82358'

(50) Latin Name: *Prunus persica*
Varietal Denomination: R82358

(76) Inventor: Michael Scott Reimer, Dinuba, CA (US)

( * ) Notice: Subject to any disclaimer, the term of this patent is extended or adjusted under 35 U.S.C. 154(b) by 373 days.

(21) Appl. No.: 12/932,925

(22) Filed: Mar. 8, 2011

(65) Prior Publication Data

US 2012/0233730 P1 Sep. 13, 2012

(51) Int. Cl.
*A01H 5/00* (2006.01)

(52) U.S. Cl.
USPC ..... Plt./190

(58) Field of Classification Search
USPC ..... Plt./190
See application file for complete search history.

(56) References Cited

U.S. PATENT DOCUMENTS

| | | | | |
|---|---|---|---|---|
| PP13,477 | P2 * | 1/2003 | Slaughter et al. | Plt./190 |
| PP13,589 | P2 * | 2/2003 | Gerdts et al. | Plt./190 |
| PP13,590 | P2 * | 2/2003 | Gerdts et al. | Plt./190 |
| PP14,363 | P2 * | 12/2003 | Gerdts et al. | Plt./190 |
| PP15,622 | P2 * | 3/2005 | Slaughter et al. | Plt./190 |
| PP15,694 | P2 * | 3/2005 | Slaughter et al. | Plt./190 |
| PP22,494 | P3 * | 2/2012 | Maillard et al. | Plt./190 |

* cited by examiner

*Primary Examiner* — Wendy C Haas
(74) *Attorney, Agent, or Firm* — Mark D. Miller

(57) ABSTRACT

A new and distinct variety of nectarine tree which is distinguished by producing fruit which are mature for harvesting and shipment August 1-5th in the San Joaquin Valley of Central California and where the fruit is high quality, very large, with good flavor and with dark red coloration over the fruit surface.

1 Drawing Sheet

Latin name: *Prunus persica.*
Varietal denomination: 'R82358'.

BACKGROUND OF THE NEW VARIETY

The present invention relates to a new variety of nectarine tree, *Prunus persica* var. nectarine, which will be named 'R82358' and more specifically as a nectarine tree which produces moderately red and dark red blush color fruit with orange flesh color and very good size which matures for commercial harvest and shipment around August 1-5 in the San Joaquin Valley of Central California. This new variety of nectarine tree has good color, good size and ability to store and ship well. Therefore, this new variety of nectarine should be a commercial success and appealing to the consumer.

ORIGIN AND ASEXUAL REPRODUCTION OF THE NEW VARIETY

The present variety of nectarine was discovered by the inventor. A shipment of seventy nectarine trees was received from a commercial nursery in the Central San Joaquin Valley and planted in Dinuba, Calif. in 2005. One of these trees, a bud sport of 'Burnectfifteen' (U.S. Plant Pat. No. 15,622), known as Summer Flare 27, produced the fruit described above. The plant was asexually reproduced by grafting onto 'Nemaguard' (unpatented) rootstock in Dinuba, Calif. and reproduces true to type in subsequent generations of asexual reproduction.

SUMMARY OF THE NEW VARIETY

The nectarine tree of the new variety is characterized by producing a fruit for commercial harvest and shipment around August 1-5 in the San Joaquin Valley of Central California.

BRIEF DESCRIPTION OF THE DRAWINGS

The drawing is a colored photograph displaying a leaf shoot with upper leaf surface at the top; to the right is a young twig (branch) and near the bottom of the twig is a stone or pit; just below the leaf shoots are two small fruit, the left one of which displays the stem end, and the right one displays a side view of the fruit; just below that are two additional fruit, the left one of which displays the suture, and the right fruit is cut to display the flesh; to the right is a large fruit displaying the blossom end; and across the bottom of the photo are two leaves displaying lower or bottom sides.

DETAILED DESCRIPTION

Referring more specifically to the horticultural details of the new and distinct variety of nectarine tree, the following has been observed under the ecological condition prevailing at the orchard of origin in the San Joaquin Valley of Central California. All major color descriptions are by reference to the Dictionary of Color by Maerz and Paul, First Edition, 1930. Common color names are also occasionally employed.

TREE

The measured tree has been pruned every winter:
Size: Approximately 12 feet high and 12 feet wide.
Vigor: Very good.
Figure: Upright and spreading.
Productivity: Very good to excellent for fifth leaf.
Regularity of bearing: Regular.

TRUNK

Size: 17 inches in circumference, 15 inches above ground.
Surface: Texture rough.

Color: (7-E-10) Chestnut Brownstone +.
Lenticels: Abundant on trunk surface, lenticular in shape, approximately 3 mm (0.12 inch) long; 1 mm (0.04 inch) width.

BRANCHES

Size: 10-12 inches in circumference, 12 inches above crotch; angle of scaffold branches—approx. 40°.
Surface texture: Mature branches moderately smooth; immature branches smooth.
Color:
*Mature branches*.—(8-L-6) Mirador Argentina + Art Brown+.
*Immature branches*.—(18-K-7) near SPRING GR.
Lenticels: 2-3 mm long (0.08-0.12 inch).

LEAVES

Length: 15.24 cm-19.05 cm (6-7.46 inches).
Width: 3.81-4.76 cm (1.5-1.875 inch).
Shape: Lanceolate.
Color:
*Upward disposed surface*.—(23-L-7) near Cypress Green.
*Downwardly disposed surface*.—(21-L-9).
Marginal form: Crenate.
Leaf margin: Slightly undulate.
Leaf midvein: Color—(18-F-3) Glass gr.
Leaf midvein thickest: 1-15. mm (0.04-0.06 inch).
Glandular characteristics: 1-3 at base of leaf; reniform shape—1.5-3 mm (0.06-0.12 inch).
Color: (15-C-2) English Grey Crag+.
Petiole:
*Length*.—8-15 mm (0.32-0.59 inch).
*Thickness*.—3 mm (0.12 inch).
*Color*.—(19-K-3) Chrysolite gr.

FLOWERS & INFLORESCENCE

Flower buds:
*Size*.—Medium — 7 mm (0.38-0.39 inch).
*Form*.—Conic with heavy grey pubescence.
Flower bud scales: Color (7-L-12) Caldera.
Flowers:
*Generally*.—Bloom starts in early March, about 40°-50° by March 2. Full bloom in third or fourth week of March. Bloom quantity should be fairly abundant with the flower buds averaging one to two per node with two the most common.
Size: Large showy type flowers.
Diameter: Fully expanded floom—35 mm (1.38 inch) to 38 mm (1.50 inch).
Petals:
*Size*.—Large.
*Length*.—15 mm (0.59 inch) to 19 mm (0.74 inch).
*Width*.—15 mm (0.59 inch) to 18 mm (0.71 inch).
*Form*.—Broadly ovate.
*Color*.—Light pink (1-A-2).
Petal claw: Broadly truncate + moderately broad.
Petal margin: Undulate especially atypically.
Petal apex: Rounded.
Pedicle:
*Length*.—2.5 mm (0.98 in).
*Thickness*.—Average 2 mm (0.78 inch).
*Color*.—(19-K-3) Chrysolite gr.
Anthers: Size—medium.
Pollen: Abundant; color yellow (9-K-2) chrome lemon.
Stamen: Length—averaging 12-15 mm (0.41-0.59 inch) and are equal or shorter than the pistil.
Filament color: (1-C-7) pink 2T, darkening with age to (2-G-3) dark pink.
Pistil:
*Length*.—Averaging 18 mm (0.71 inches) including oval.
*Color*.—(17-N-3) light yellow green.
*Surface*.—Pistil and ovary are glabrous.

FRUIT

Ripe for commercial harvest and shipment: August 1-5.
Size: Large—4 fruit weigh 3 lbs.—Avg. 1206 (340.68 grams).
Diameter in the axial plane: 7.30-7.94 cm (2.875-3.125 inch).
Transverse in the suture plane: 7.94-8.89 cm (3.125-3.5 inch).
Transverse at right angles to the suture plane: 7.30-7.94 cm (2.875-3.125 inch).
Form:
*Uniformity*.—Uniform.
*Symmetrical or asymmetrical*.—Symmetrical.
*Suture*.—From apex to base — visible and moderate.
*Ventral surface*.—Smooth.
Stem: Short: 5-6 mm (0.20-0.24 inch).
Caliper: 0.5 mm (0.20 inch).
Apex: Rounded.
Pistil point: Oblique.

SKIN/FLESH

Thickness: Normal for nectarines.
Texture: Firm, glabrous.
Tendency to crack: None observed.
Color code:
*Blush color*.—(5 L-11) Brickdust to (55-L-8) Rubient.
*Ground color*.—(9 L-6) Golden Glow.
*Flesh color*.—(9-L-5) — near apricot.
Juice production: Moderate to heavy.
Flavor: Very good.
Aroma: Mild.
Fibers: Few, texture firm.
Ripening: Even.
Eating quality: Very good.

STONE

Free or clingstone: Clingstone.
Fibers: On both sides of stone—approx. 4-5 mm (0.16 - 0.20 inch).
Size: Medium large.
*Length*.—41 mm (1.61 inches) to 34 mm (1.3 inches).
*Width*.—28 mm (1.10 inches) to 28 mm (1.10 inches).
*Thickness*.—22 mm (0.87 inches) to 20 mm (0.79 inch).
Form: Ovate.
Apex shape: Rounded to acute.
Color: Ridges are (56-J-12) Port Wine, while remainder of stone is (50-K-7) Persian Rose.
Base: Rounded with slanted sides.
Hilum: Ovate.
Ridge: Heavy throughout the stone, dorsal more tightly grooved.
Tendency to spin: None observed.
Use: Fresh market.

Keeping and shipping quality: Very good.
Resistance to disease: None known.
Harvesting and shipping: August 1-5$^{th}$.

Although the new variety of nectarine tree has the desired characteristics described above that are the result of the growing conditions prevailing near the town of Dinuba in the San Joaquin Valley of Central California, it is to be understood that variation of the usual magnitude may occur due to changes in growing conditions such as irrigation, fertilization, pruning, pesticide, disease control, climatic variations.

Having thus described and illustrated the new variety of nectarine tree, what is claimed as new and desired to be secured by Plant Letter Patent is:

1. A new variety of nectarine which is distinguished by producing fruit which is mature for commercial harvesting and shipment around August 1-5th in the San Joaquin Valley of Central California which is characterized by very large fruit with a distinct intense red color over the fruit surface.

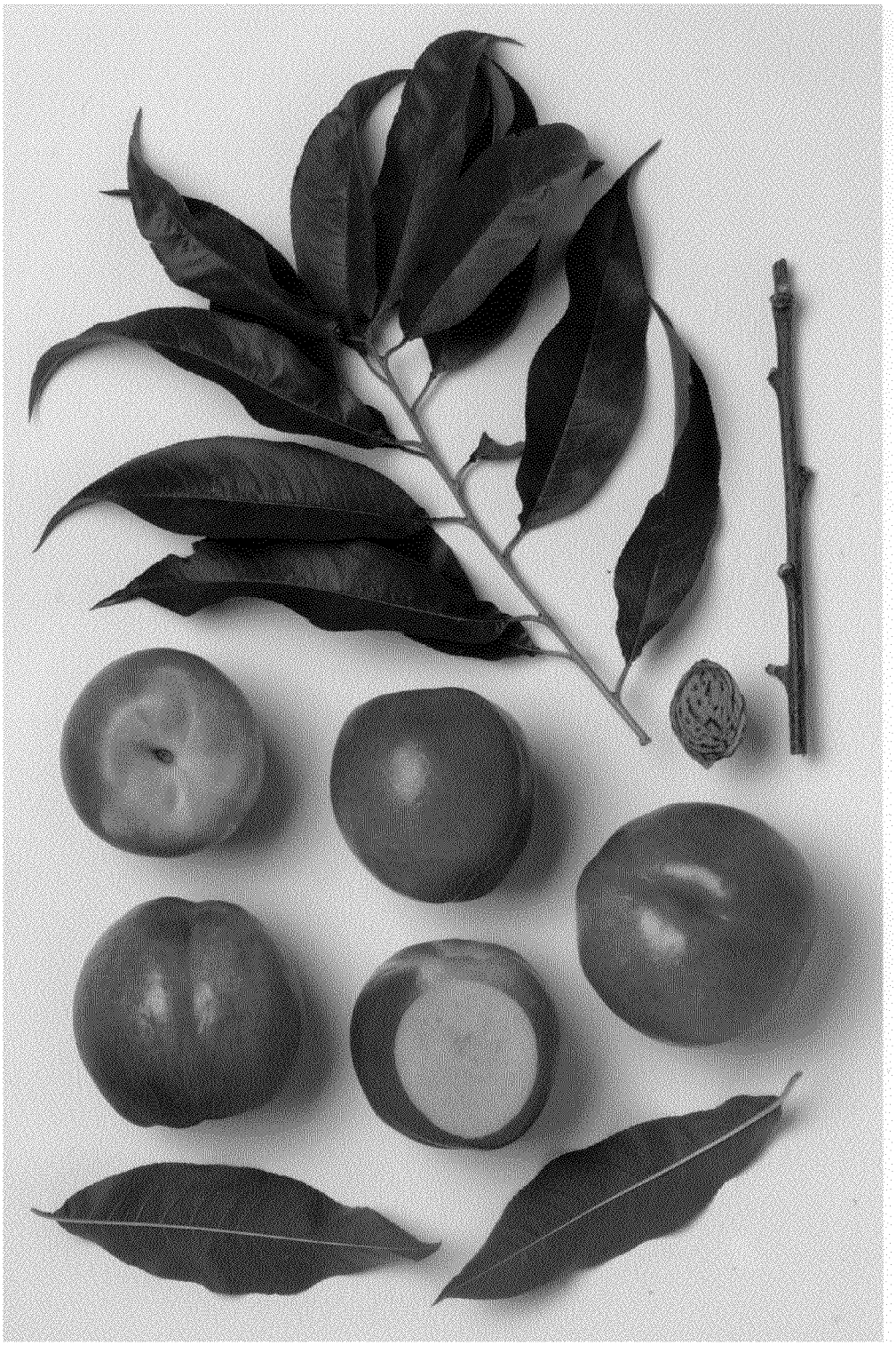

* * * * *